United States Patent [19]

Southwick et al.

[11] Patent Number: 4,981,977

[45] Date of Patent: Jan. 1, 1991

[54] INTERMEDIATE FOR AND FLUORESCENT CYANINE DYES CONTAINING CARBOXYLIC ACID GROUPS

[75] Inventors: Philip L. Southwick; Alan S. Waggoner, both of Pittsburgh, Pa.

[73] Assignee: Carnegie-Mellon University, Pittsburgh, Pa.

[21] Appl. No.: 364,773

[22] Filed: Jun. 9, 1989

[51] Int. Cl.$^5$ .................. C07D 403/06; C07D 209/02
[52] U.S. Cl. ..................................... 548/455; 548/510
[58] Field of Search .............................. 548/455, 510

[56] References Cited

U.S. PATENT DOCUMENTS

| | | | |
|---|---|---|---|
| 4,394,314 | 7/1983 | Peterson | 548/455 |
| 4,419,511 | 12/1983 | Rame | 548/455 |
| 4,847,385 | 7/1989 | Kusakata | 548/455 |

*Primary Examiner*—David B. Springer
*Attorney, Agent, or Firm*—Cohen & Grigsby

[57] ABSTRACT

(2,3,3-Trimethyl-3-H-indol-5-yl)-acetic acid has been synthesized. Additionally, derivatives of (2,3,3-Trimethyl-3-H-indol-5-yl)-acetic acid have been prepared as intermediates for preparation of fluorescent cyanine biolabels. A derived dye, 5.5'-Dicarboxymethyl-3,3,3',3'-tetramethyl-1,1'-diethylindocarbocyanine, is a biolabeling substance with a brilliant red fluorescence.

12 Claims, No Drawings

INTERMEDIATE FOR AND FLUORESCENT CYANINE DYES CONTAINING CARBOXYLIC ACID GROUPS

FIELD OF THE INVENTION

This invention relates to carboxy cyanine dyes and, more particularly, to the synthesis of (2,3,3-Trimethyl-3-H-indol-5-yl)-acetic acid and its derivatives as intermediates for preparation of cyanine dyes.

BACKGROUND OF THE INVENTION

Highly fluorescent carboxyl-containing indocyanine dyes are useful as labeling reagents for biological investigations. Functional groups on the dyes permit covalent bonding to biomaterials and/or nonbiological materials for purposes of fluorescence detection of the labeled material and, depending upon the functional groups, such covalent bonding can be selective. See Alan S. Waggoner, "Fluorescent Probes for Analysis of Cell Structure, Function, and Health by Flow and Imaging Cytometry"; Applications of Fluorescence in the Biomedical Sciences, pages 3-28, 1986 Alan R. Liss, Inc. Depending upon the material, dyes containing selected functional groups will or will not bind to the material. The incorporation of carboxylic acid groups into the basic cyanine structure is expected to permit fluorescent labeling through the use of derived active esters. Thus, it is of interest to synthesize compounds containing carboxylic acid groups that will provide for the construction of the carboxyl-containing indocyanine dyes.

(2,3,3-Trimethyl-3-H-indol-5-yl)-acetic acid (3) is expected to possess exceptional advantages as the precursor of a family of dyes of cyanine and related types intended for use as covalently attached fluorescent labels for biological research. Disclosed herein is a convenient synthesis of 3 and its conversion to derivatives used to prepare carboxy cyanines.

Because the hydrazone 2 deteriorated rapidly during storage, attention was directed to "one pot" versions of the Fischer synthesis. However, procedures in the prior art proceeded slowly and gave poor yields of 3. See B. Robinson, "The Fischer Indole Synthesis," John Wiley & Sons, Inc., New York, N.Y. (1985) p. 640. It was found that, in acetic acid, hydrazone formation is nearly complete within 30 minutes in the presence of acetate ion. Indolization to 3 (UV max 260 nm) is essentially complete after 30 minutes at reflux. The generation of small amounts of a purple-red by-product often accompanied indolization, generally to a greater extent when sodium acetate had been added than when it had not. Yields of recrystallized product of satisfactory purity were 60% based on the arylhydrazine hydrochloride 1.

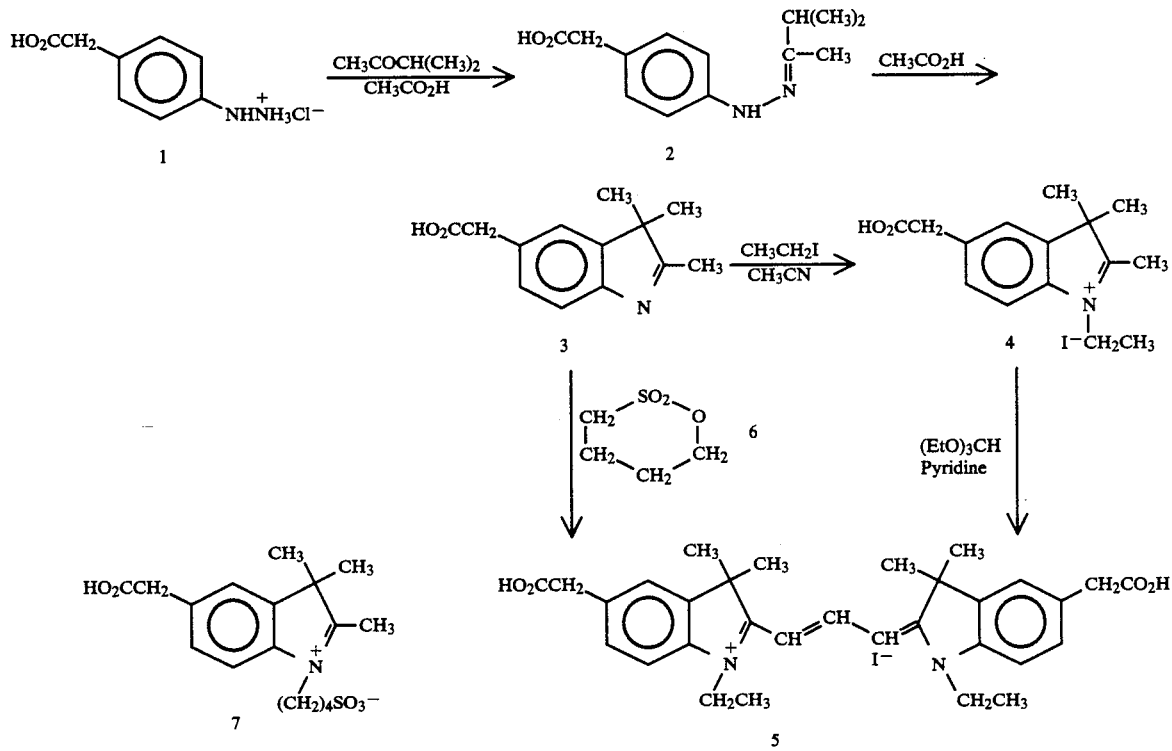

Compound 3 is a fluorescent substance; its solutions produce spots with a blue-white fluorescence on thin-layer plates when irradiated at 360 nm. Reaction with ethyl iodide yielded the ethiodide 4, which was converted to the highly fluorescent carbocyanine 5 (red fluorescence) by treatment with triethyl orthoformate in refluxing pyridine. See F. M. Hamer, J. Chem. Soc., 2796 (1927) for the examples of this method. Reaction of 3 with 1,4-butanesultone 6) afforded 7, a type of quaternary salt useful as an intermediate for water-soluble cyanine dyes. See United Kingdom Patent No. 742,112 (1955), Agfa A. G. fur Photofabriken; Chemical Abstracts, 50, 111496 (1956).

SUMMARY OF THE INVENTION

The present invention relates to (2,3,3-Trimethyl-3-H-indol-5-yl)-acetic acid which is a useful precursor for a family of dyes of cyanine and related types to form cyanine dyes with a functional group to provide for covalent attachment to biomaterials.

The present invention also relates to substituted (2,3,3-Trimethyl-3-H-indol-5-yl)-acetic acid compounds which can be converted to fluorescent cyanine dyes. The substituted (2,3,3-Trimethyl-3-H-indol-5-yl)-acetic acid compounds are represented by the formula

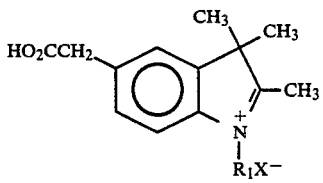

where $R_1$ is —$(CH_2)_mCH_3$, m ranging from 0 to 25, or arylalkyl and $X^-$ is a counterion. The counterion may be F, Cl, Br, or I or $R_2SO_3^-$, where $R_2$ is alkyl, aryl, or arylalkyl. Additionally, an internal carboxylate salt may be the counterion.

The present invention also relates to other substituted (2,3,3-Trimethyl-3-H-indol-5-yl)-acetic acid compounds represented by the formula

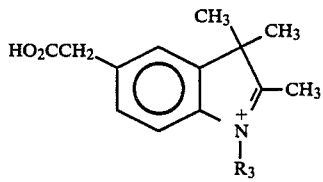

where $R_3$ is —$(CH_2)_l$ COOH $Y^-$, l ranging from 1 to 5; —$(CH_2)_nSO_3^-$, n ranging from 2 to 6; or —$(CH_2)_kN^+(R_4)_3Z^-$, k ranging from 1 to 4 and $R_4$ is —$(CH_2)_jCH_3$, j ranging from 0 to 25, or H, and where $Y^-$ and Z are the appropriate counterions. The $Y^-$ counterion may be F, Cl, Br or I or $R_5SO_3^-$ or $SO_4^=$, where $R_5$ is alkyl, aryl, arylalkyl or H. The Z counterion may be F, Cl, Br, I, $R_5SO_3^-$ or $SO_4^=$. Many other counterions are possible depending on the method of synthesis and the components included in the solvents used to isolate and pur.fry the organic compound.

Particularly, the present invention relates to (2,3,3-Trimethyl-3-H-indol-5-yl)-acetic acid Ethiodide as represented by the formula

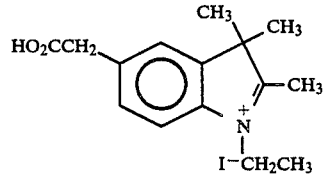

Particularly, the present invention also relates to 5-Carboxymethyl-2,3,3-trimethyl-3-H-indolium-1-(4'-sulfobutyl)betaine as represented by the formula

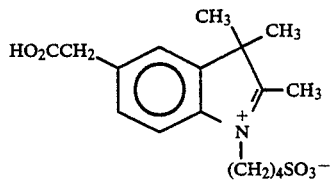

In addition, the present invention relates to a cyanine dye, 5,5'-Dicarboxymethyl-3,3,3',3 -tetramethyl-1'-diethylindocarbocyanine Iodide, represented by the following formula, made from a substituted (2,3,3-Trimethyl-3-H-indol-5-yl)-acetic acid compound

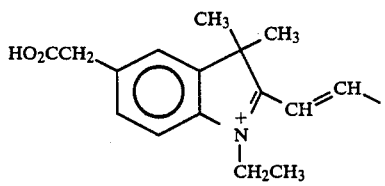

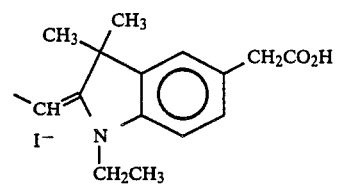

DETAILED DESCRIPTION OF PREFERRED EMBODIMENTS AND EXAMPLES

The hydrochloride of p-carboxymethylphenylhydrazine (1) was made through the diazotization of p-aminophenylacetic acid and subsequent reduction according to the procedure set forth in I. M. Hunsberger, E. R. Shaw, J. Fugger, R. Ketcham and R. Lednicer, *J. Org. Chem.*, 21, 294 (1956).

(2,3,3-Trimethyl-3-H-indol-5-yl)-acetic acid (3).
Procedure A (Acetic acid and potassium acetate).

The hydrochloride of p-carboxymethylphenylhydrazine (1) (6.06 g, 30 mmol) and potassium acetate (6.0 g, 60 mmol) were suspended in a mixture of methyl isopropyl ketone (3.7 g, 42 mmol) and glacial acetic acid (30 ml). The mixture was stirred at room temperature for 30 min. A spectrum taken on a sample withdrawn from the mixture at this time showed the strong absorption at 275 nm of the phenylhydrazone (2) and the 232 nm maximum of the hydrazine (1) was absent. The mixture was then stirred and heated at reflux for 1 hr. By that time the maximum at 275 nm had disappeared and been replaced by the 260 nm maximum of 3. Removal of the solvent under reduced pressure on a rotary evaporator left a residue, which solidified when triturated with water (20 ml). It was collected and recrystallized from ethyl acetate to give 3.89 g (60%) of crystals with a yellow-brown tint, mp. 155°–165°. An additional crystallization from ethyl acetate gave flat needles with a light tan tint, mp. 168°–170° C.

$^1$H-NMR (CDCl$_3$): δ 1.25 (s, 6H, 3-methyls), 2.25 (s, 3H, 2-methyl), 3.60 (s, 2H, methylene of 5-carboxymethyl), 7.15–7.56 ppm (m, 3H, benzene ring). Anal. Calcd. for C$_{13}$H$_{15}$NO$_2$: C, 71.86; H, 6.96;N, 6.45. Found: C, 71.69; H, 6.97; N, 6.41.

Procedure B
(Acetic acid)

A mixture containing 1 (6.06 g, 30 mmol), methyl isopropyl ketone (3.7 g, 42 mmol) and acetic acid (30 ml) was stirred for 30 min. at room temperature; at this point the UV spectrum of the solution showed hydrazone formation to be incomplete. The mixture was then stirred and heated at reflux for 30 additional min., at which time the spectrum coincided with that of 3 (maximum at 260 nm). The product, mp. 163°-170°, was isolated as described above in 61% yield (3.95 g).

(2,3,3-Trimethyl-3-H-indol-5-yl)-acetic acid Ethiodide (4).

Compound 3 (0.5 g, 2.3 mmol) was suspended in a mixture of acetonitrile (5 ml) and ethyl iodide (2 g, 12.8 mmol) and the mixture was refluxed with stirring for 1 hr. More ethyl iodide (2 g) was then added, and heating and stirring were continued for an additional 5 hrs. The mixture was then cooled and diluted with ether (20 ml). The precipitated deliquescent product was collected by gravity (not suction) filtration and washed on the filter with isopropyl alcohol (10 ml), yield 0.42 g (49%) of 4, mp. 210°-217° C. (dec.). Recrystallization, effected by diluting a concentrated methanol solution with isopropyl alcohol to cloudiness, afforded colorless flakes; mp. 217° (dec.) with shrinking from 205° C.

$^1$H-NMR (CDC$_3$-CF$_3$CO$_2$H): δ 1.60 (s+t, 9H, 3-methyls (s) coinciding with methyl (t) of 1-ethyl), 2.85 (s, 3H, 2-methyl), 3.90 (s, 2H, methylene of 5-carboxymethyl), 4.54 (q, 2H, methylene of 1-ethyl), 7.60 ppm (center of multiplet) (m, 3H, benzene ring). Anal. Calcd. for C C, 48.27; H, 5.40; N, 3.75. Found: C, 48.38 H, 5.41 N, 3.71.

5.5'-Dicarboxymethyl-3,3,3', 3'-tetramethyl-1,1'-diethylindocarbocyanine Iodide (5)

A solution of ethiodide 4 (0.373 g, 1.0 mmol) and triethyl orthoformate (0.44 g, 3.0 mmol) in pyridine (5 ml), was heated at reflux for 1 hr. The mixture turned a deep purple-red color within the first few minutes of heating. The pyridine was removed under reduced pressure using a rotary evaporator. The solid residue was dissolved in warm methanol (4 ml) and 15 ml of 0.067 N hydriodic acid (1.0 mmol) was added with stirring to precipitate 0.265 g (84%) of the product as a dark-purple powder. It was recrystallized by adding 0.1 N aqueous hydriodic acid to a solution of the dye in methanol until the product separated in the form of a granular blue-black crystalline precipitate, mp. 250°-253° C. (dec.).

IR (Nujol): 3400 (broad), 2900 (broad), 1725, 1613, 1555, 1450, 1420, 1370, 1335, 1270, 1245, 1190, 1160, 1140, 1112, 1080, 1070, 1030 925 780 cm$^{-1}$. Visible spectrum (ethanol): λ$_{max}$(log ε) 530 (4.97), 564 nm; (5.13). Fluorescence spectra (ethanol): emission maximum, 580 nm; excitation maxima, 532 (shoulder), 565 nm. When spotted on TLC plates, 5 shows a brilliant red fluorescence under irradiation at 360 nm. Reversed-phase silica-gel plates (Analtech RPS-F) were used with carboxyl-containing cyanines, with development by methanol-water or acetone-water mixtures. Anal. Calcd. for C$_{31}$H$_{37}$IN$_2$O$_4$: C, 59.24; H, 5.93; N, 4.45; I, 20.19. Found: C, 60.35; H, 6.20; N, 4.52; I, 18.51.

F. M. Hamer, in *J. Chem. Soc.*, 2796 (1927) reported that samples of a dye of the same indocarbocyanine series as 5 also showed a low iodine content. Apparently recrystallizations of these cyanine dyes in the presence of water may yield products in which iodide ion is partly replaced by another anion. In the case of 5, loss of iodide ion together with a proton from the carboxyl would produce a betaine. The iodine content of this analyzed sample would correspond to that of a mixture consisting of 5 (91.7%) and 8.3% of an iodine-free form of the dye. If 5 and the betaine were present in that proportion, the calculated values would be C, 60.48; H, 6.04; N, 4.55; I, 18.51, in quite good agreement with the values found.

5-Carboxymethyl-2,3,3-trimethyl-3-H-indolium-1-(4'-sulfobutyl)betaine (7)

Compound 3 (1.0 g, 4.61 mmol) was dissolved in hot n-butyronitrile (10 ml) and 1,4-butanesultone 6 (1.0 g, 7.35 mmol) was added. The mixture was stirred and maintained under reflux for 22 hrs (bath at 123° C.). During this time, the product separated as a crystalline powder. The mixture was cooled, diluted with ether (35 ml), and the product was collected as a light-brown granular powder, mp. 285°-288° C.; yield: 1.0 g (61%). Dilution of a hot methanol solution of 7 with isopropyl alcohol afforded granular crystals with a light purple tint, mp. 287°-290° C.

$^1$H-NMR (CDCl$_3$-CF$_3$CO$_2$H): δ 1.61 (s, 6H, 3-methyls), 2.00-2.40 (m, 4H, 2'- and 3'-methylenes of butyl), 2.81 (s, 3H, 2-methyl), 3.20-3.45 (m, 2H, 4'-methylene of butyl), 3.90 (s, 2H, methylene of carboxymethyl), 4.30-4.60 (m, 2H, 1'-methylene of butyl), 7.45-7.75 ppm (m, 3H, benzene ring). Anal. Calcd. for C$_{17}$H$_{23}$NO$_5$S: C, 57.77; H, 6.56; N, 3.96. Found: C, 57.59; H, 6.61; N, 3.95.

Those of ordinary skill in the art will appreciate that variations of (2,3,3-Trimethyl-3-H-indol-5-yl)-acetic acid Ethiodide can be made where compound 3 is reacted with compounds such as p-toluenesulfonic acid, ethylbenzenesulfonate and ethanesulfonic and, in addition, various monohalogenated alkyl or arylalkyl compounds. It will also be appreciated by those of ordinary skill in the art, through mechanisms well known to the art, that substituted (2,3,3-Trimethyl-3-H-indol-5-yl)-acetic acid can form an internal carboxylate salt, that is, the counterion is internal to the compound.

Further, other substituted (2,3,3-Trimethyl-3-H-indol/5-yl)-acetic acid compounds can be made by reacting (2,3,3-Trimethyl-3-H-indol-5-yl)-acetic acid with, for example, monohaloacetic acid (ACH$_2$COOH, where A can be F, Cl, Br or I), 4-halobutanoic acid, or a tetraalkylammonium salt in which one alkyl group carries a halogen atom displaceable to form a counterion.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

WHAT IS CLAIMED IS:

1. The compound having the formula

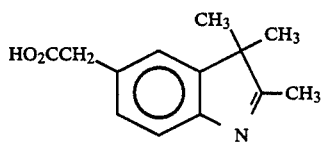

2. The compound having the formula

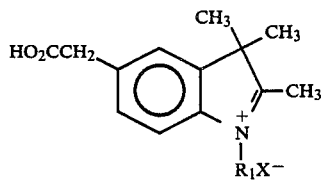

where $R_1$ is —$(CH_2)_m CH_3$, m ranging from 0 to 25, or arylalkyl and $X^-$ is a counterion to $N^+$.

3. The compound of claim 2 wherein said counterion consists of $F^-$, $Cl^-$, $Br^-$ or $I^-$.

4. The compound of claim 2 wherein said counterion consists of $R_2SO_3^-$ where $R_2$ is alkyl, aryl, arylalkyl, or OH.

5. The compound of claim 2 wherein said counterion is an internal carboxylate salt.

6. The compound having the formula

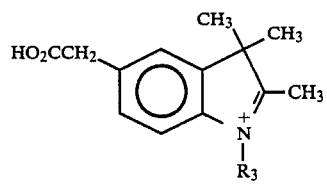

where $R_3$ is —$(CH_2)_m COOH\ Y^-$, m ranging from 1 to 5, —$(CH_2)_n SO_3^-$, n ranging from 2 to 6, or —$(CH_2)_k N^+(R_4)_3 Z$, k ranging from 1 to 4 and $R_4$ is —$(CH_2)_j CH_3$, j ranging from 0 to 25, or H, where $Y^-$ and $Z^-$ are appropriate counterions to $N^+$.

7. The compound of claim 6 wherein said $Y^-$ counterion consists of $F^-$, $Cl^-$, $Br^-$ or $I^-$.

8. The compound of claim 6 wherein said $Y^-$ counterion consists of $R_5SO_3^-$ where $R_5$ is alkyl, aryl, arylalkyl or OH.

9. The compound of claim 6 where said $Z^-$ counterion is $F^-$, $Cl^-$, $Br^-$, $I'$ or $RSO_3^-$.

10. The compound having the formula

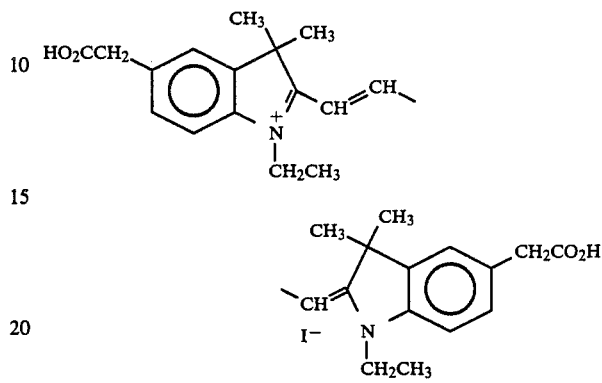

11. The compound having the formula

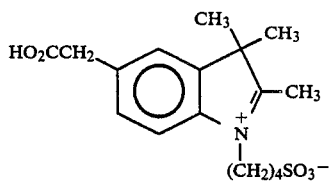

12. The compound having the formula

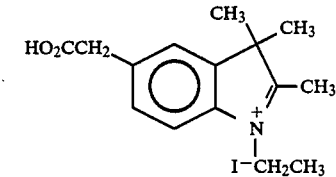

* * * * *

UNITED STATES PATENT AND TRADEMARK OFFICE
CERTIFICATE OF CORRECTION

PATENT NO. : 4,981,977

DATED : January 1, 1991

INVENTOR(S) : Philip L. Southwick, Alan S. Waggoner

It is certified that error appears in the above—identified patent and that said Letters Patent is hereby corrected as shown below:

Column 3, line 22, change "F, Cl, Br, or I" to -- $F^-$, $Cl^-$, $Br^-$, or $I^-$ -- ;

Column 3, line 44, change "and z" to -- and $z^-$ -- ;

Column 3, line 45, change "F, Cl, Br or I" to -- $F^-$, $Cl^-$, $Br^-$ or $I^-$ -- ;

Column 3, line 46, change "z" to -- $z^-$ -- ;

Column 3, line 47, change "F, Cl, Br, I," to -- $F^-$, $Cl^-$, $Br^-$, $I^-$, -- .

Column 7, line 40, change "$-(CH_2)_kN+(R_4)_3Z$" to -- $-(CH_2)_kN+(R_4)_3Z^-$ -- .

UNITED STATES PATENT AND TRADEMARK OFFICE
CERTIFICATE OF CORRECTION

PATENT NO. : 4,981,977
DATED : January 1, 1991
INVENTOR(S) : Philip L. Southwick, Alan S. Waggoner It is certified that error appears in the above—identified patent and that said Letters Patent is hereby corrected as shown below:

Columns 1 and 2, lines 18-49, change:

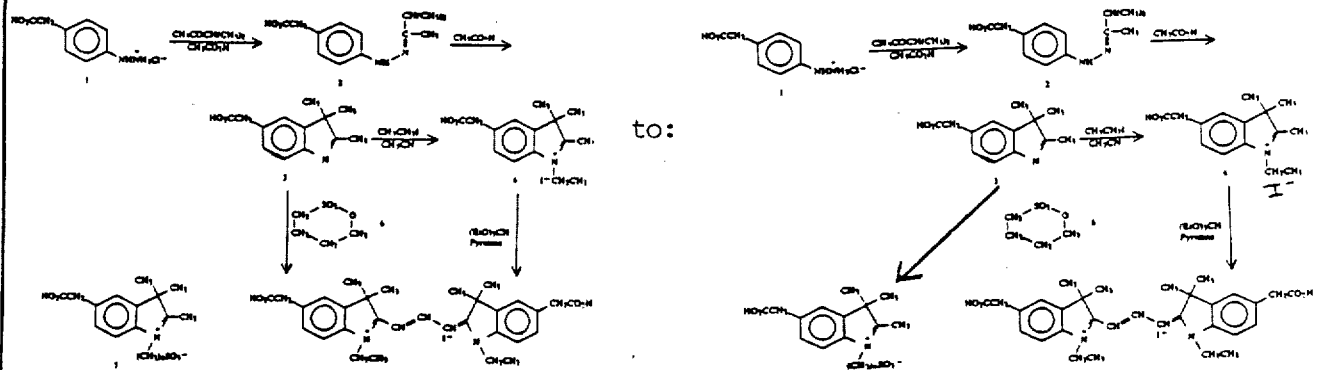

UNITED STATES PATENT AND TRADEMARK OFFICE
CERTIFICATE OF CORRECTION

Page 3 of 3

PATENT NO. : 4,981,977
DATED : January 1, 1991
INVENTOR(S) : Philip L. Southwick, Alan S. Waggoner It is certified that error appears in the above-identified patent and that said Letters Patent is hereby corrected as shown below:

Column 3, line 60, change:

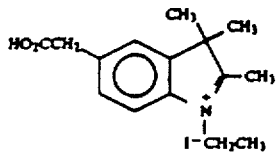     to:     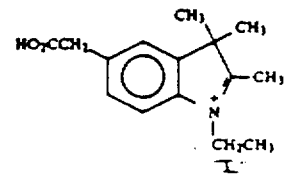

Column 9, line 14, change:

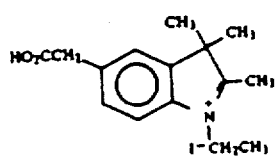     to:     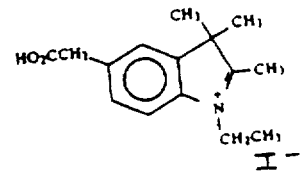

Signed and Sealed this

Fourth Day of August, 1992

Attest:

DOUGLAS B. COMER

Attesting Officer

Acting Commissioner of Patents and Trademarks